United States Patent [19]

Grinter et al.

[11] Patent Number: 5,017,701
[45] Date of Patent: May 21, 1991

[54] PROCESS FOR THE PREPARATION OF PURINE DERIVATIVES

[75] Inventors: Trevor J. Grinter, Betchworth; Peter M. Kincey, Epsom, both of England

[73] Assignee: Beecham Group, p.l.c., Brentford, England

[21] Appl. No.: 383,859

[22] Filed: Jul. 21, 1989

[30] Foreign Application Priority Data

Jul. 23, 1988 [GB] United Kingdom ............... 8817607

[51] Int. Cl.$^5$ .................. C07D 473/38; C07D 473/40
[52] U.S. Cl. ...................................... 544/276; 544/277
[58] Field of Search ............................... 544/276, 277

[56] References Cited

U.S. PATENT DOCUMENTS

| 4,347,185 | 8/1982 | Muchowski et al. | 548/516 |
|-----------|--------|------------------|---------|
| 4,347,187 | 8/1982 | Muchowski et al. | 548/453 |
| 4,798,833 | 1/1989 | Johansson et al. | 514/262 |
| 4,845,084 | 7/1989 | Hannah et al.    | 514/81  |

FOREIGN PATENT DOCUMENTS

| 0182024 | 5/1986 | European Pat. Off. | 544/277 |
|---------|--------|---------------------|---------|
| 0302644 | 2/1989 | European Pat. Off. | 544/265 |
| WO87/5604 | 9/1987 | PCT Int'l Appl. | 544/277 |

OTHER PUBLICATIONS

Padgett et al., J. Org. Chem., vol. 44, No. 20, pp. 3492-3496 (1979).
Csendes et al., J. Org. Chem., vol. 44, No. 23, pp. 4173-4178 (1979).

*Primary Examiner*—Diana Rivers
*Attorney, Agent, or Firm*—Hopgood, Calimafde, Kalil, Blaustein & Judlowe

[57] ABSTRACT

A process for the preparation of a compound of formula (I) or a pharmaceutically acceptable salt thereof:

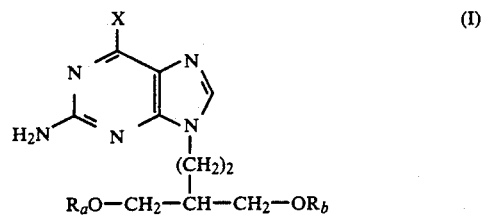

which process comprises reacting a compound of formula (II):

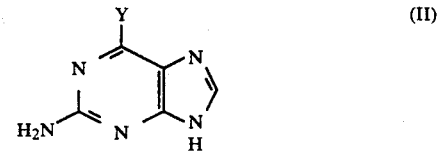

wherein the amino group is optionally protected, Y is iodo, optionally substituted benzylthio or (phenacylmethyl)thio, with a compound of formula (III):

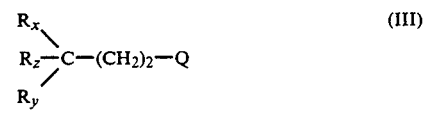

wherein Q is a leaving group, $R_x$ and $R_y$ are protected hydroxymethyl or acyloxymethyl, or group(s) convertible to hydroxymethyl or acyloxymethyl; and $R_z$ is hydrogen or a group convertible thereto; and thereafter converting Y to X is hydroxy by means of hydrolysis, or to X is hydrogen by means of reduction; converting $R_x$ and $R_y$ when other than hydroxymethyl or acyloxymethyl, to hydroxymethyl or acyloxymethyl, optionally converting $R_x/R_y$ hydroxymethyl to acyloxymethyl or vice versa, deprotecting the 2-amino group where necessary and converting $R_z$, (when other than hydrogen) to hydrogen; and optionally forming a pharmaceutically acceptable salt thereof.

8 Claims, No Drawings

PROCESS FOR THE PREPARATION OF PURINE DERIVATIVES

The present invention relates to a novel process for the preparation of purine derivatives which have antiviral activity. EP-A-141927 and EP-A-182024 (Beecham Group p.l.c.) describe, inter alia, compounds of formula (I) and pharmaceutically acceptable salts thereof:

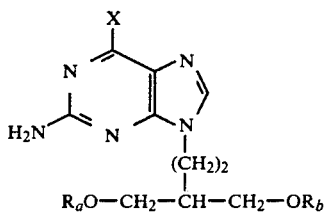

wherein X is hydrogen or hydroxy and $R_a$ and $R_b$ are independently hydrogen or a group RCO- wherein R is phenyl or $C_{1-18}$ alkyl.

The compounds of formulae (A) and (B); wherein X is OH and $R_a$ and $R_b$ are both hydrogen (BRL 39123); and wherein X is hydrogen and $R_a$ and $R_b$ are both acetyl (BRL 42810), are of particular interest as potential antiviral agents.

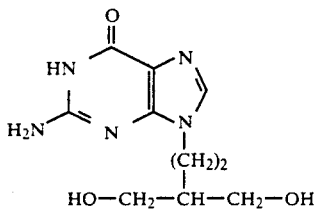

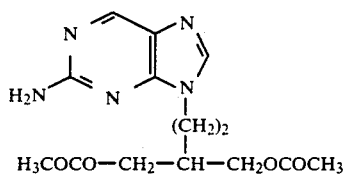

The process already described for the preparation of the above compounds involves the reaction of 2-amino-6-chloropurine of formula (C):

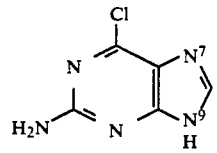

with a side chain intermediate of formula (D):

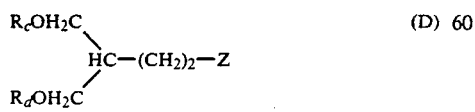

wherein $R_c$ and $R_d$ are independently acyl groups or hydroxy protecting groups and Z is a leaving group, such as halo, for example chloro, bromo, iodo; and thereafter converting the 6-chloro group to hydroxy by means of hydrolysis, or to hydrogen by means of reduction.

The disadvantage with this process is that the use of the intermediate of formula (C) results in a mixture of products i.e. that when the side chain is attached at N-9 and the undesired product wherein the side chain is attached at N-7. This can result in low yields of the desired N-9 product.

It has surprisingly been discovered that, if the 6-chloro group in the compound of formula (C) is replaced by an iodo group, a benzylthio group or a (phenacylmethyl)thio group, the ratio of N-9 product to N-7 product is increased, providing a better overall yield of the resulting compound of formula (I).

Accordingly, the present invention provides a process for the preparation of a compound of formula (I) as hereinbefore defined, or a pharmaceutically acceptable salt thereof, which process comprises reacting a compound of formula (II):

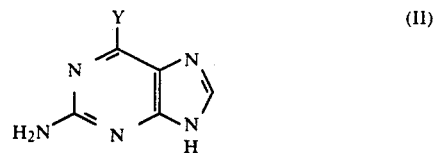

wherein the amino group is optionally protected, Y is iodo, optionally substituted benzylthio or (phenacylmethyl)thio, with a compound of formula (III):

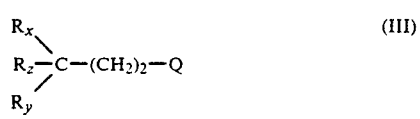

wherein Q is a leaving group, $R_x$ and $R_y$ are protected hydroxymethyl or acyloxymethyl, or group(s) convertible to hydroxymethyl or acyloxymethyl; and $R_z$ is hydrogen or a group convertible thereto; and thereafter converting Y to X is hydroxy by means of hydrolysis, or to X is hydrogen by means of reduction; converting $R_x$ and $R_y$ when other than hydroxymethyl or acyloxymethyl, to hydroxymethyl or acyloxymethyl, optionally converting $R_x/R_y$ hydroxymethyl to acyloxymethyl or vice versa, deprotecting the 2-amino group where necessary and converting $R_z$, (when other than hydrogen) to hydrogen; and optionally forming a pharmaceutically acceptable salt thereof.

The intermediates formed in this reaction are of formula (IV):

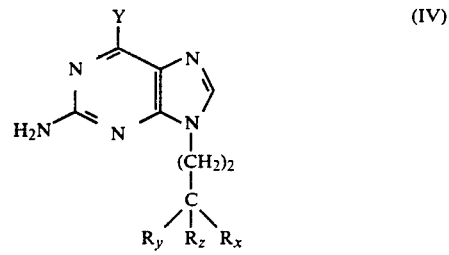

which are novel and from an aspect of the invention.

The reaction may be carried out in an inert solvent, for example dimethylformamide, dimethylsulphoxide or acetonitrile, preferably dimethylformamide, in the presence of an inorganic or organic base, over a temperature range from 0° C. to the boiling point of the solvent, usually 30°–40° C. Examples of inorganic bases include alkali metal hydrides, alkali metal carbonates such as sodium or potassium carbonate and preferably potassium carbonate. Suitable organic bases are 1,8-diazabicyclo[5 4.0]undec-7-ene and tetramethyl guanidine.

Suitable examples of optional substituents in the phenyl group Y when benzylthio or (phenacylmethyl)thio, include one or two groups selected from $C_{1-4}$ alkyl, halo and $C_{1-4}$ alkoxy. Halo includes iodo, bromo, chloro and fluoro, and alkyl/alkoxy groups include those containing methyl, ethyl, n and iso-propyl. Y may also be diphenylmethylthio, optionally substituted in the phenyl ring(s) as defined for Y when benzylthio. Y is preferably iodo or benzylthio, most preferably iodo.

Suitable examples of the leaving group Q, include halo, such as chloro, bromo or iodo, and tosyloxy and mesyloxy.

Suitable examples of hydroxy protecting groups (other than acyl groups) include the t-butyl dimethylsilyl group removable by 80% acetic acid at elevated temperatures, around 90° C., or by treatment with tetrabutyl ammonium fluoride in a solvent, such as tetrahydrofuran, at ambient temperature.

Another suitable protecting group is wherein the two hydroxy groups in formula (III) (when $R_x$ is hydroxymethyl) are reacted with 2,2-dimethoxypropane, forming a 1,3-dioxan ring. This group may be removed by acidic hydrolysis.

Other suitable protecting groups include substituted benzyl groups such as p-methoxybenzyl, removable by treatment with 2,3-dichloro-5,6-dicyanobenzoquinone.

Other suitable protecting groups are apparent to those skilled in the art.

$R_x$ and/or $R_y$ may be acyloxymethyl, such as a group $RCO_2CH_2$ wherein R is as defined in formula (I). Examples of R include methyl, ethyl, n- and iso-propyl, n- and iso-, sec- and tert-butyl, preferably methyl.

Interconversion of $R_x/R_y$ acyloxymethyl and hydroxymethyl may be carried out conventionally as described in EP-A-141927.

Other suitable values of $R_x$, $R_y$, $R_z$ include wherein the compound of formula (III) is of formula (IIIA) or (IIIB):

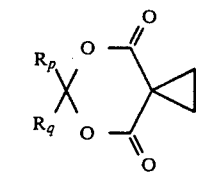

(IIIA)

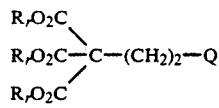

(IIIB)

wherein $R_p$ and $R_q$ are independently hydrogen, $C_{1-6}$ alkyl or phenyl, or $R_p$ and $R_q$ together are $C_{4-6}$ polymethylene; and $R_r$ is $C_{1-6}$ alkyl or phenyl $C_{1-6}$ alkyl, in which any phenyl moieties are optionally substituted, (as defined for Y hereinbefore when thiobenzyl).

When the compound of formula (IIIA) is used, the resulting intermediate is of formula (IVA):

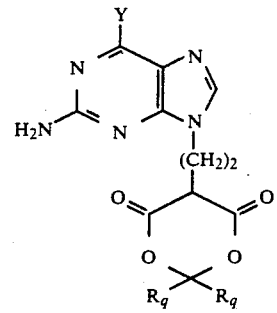

(IVA)

When the compound of formula (IIIB) is used, the resulting intermediate is of formula (IVB):

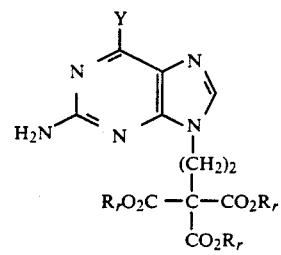

(IVB)

Values for $R_p$ and $R_q$ and $R_r$ include these values listed as suitable for R in formula (I), preferably methyl for $R_p$ and $R_q$ and ethyl for $R_r$. In addition $R_p$ and $R_q$ may together be $C_4$ or $C_5$ polymethylene.

The intermediates of formulae (IVA) and (IVB) are subsequently converted to an intermediate of formula (V):

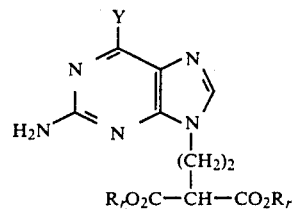

(V)

by transesterification and hydrolysis/decarboxylation respectively, as described in the Examples hereinafter.

An intermediate of formula (V) is convertible to a compound of formula (VI):

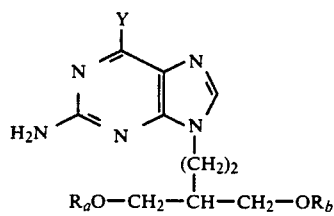

(VI)

by reduction, under conventional conditions using, for example, sodium borohydride.

It is preferred, however, that the intermediate of formula (III) is of formula (III)':

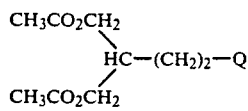
(III)' for the preparation of compounds of formula (A) and (B) as defined, because:
(i) Compounds of formula (III)' give a particularly good N9:N7 ratio (regioselectivity).
(ii) Ease of separation of N9:N7 isomers.
(iii) The same intermediate of formula (III)' is used for the preparation of compounds of the formula (A) and formula (B).

The 2-amino group may be protected, for example, using a benzyl protecting group, removable by hydrogenolysis. It may also be protected by an acyl group, for example acetyl, removable by hydrolysis, or a schiff's base, eg benzylidene, removable by acid hydrolysis.

Pharmaceutically acceptable salts are formed conventionally.

Intermediates of formula (III) wherein $R_x/R_y$ are protected hydroxymethyl or acyloxymethyl may be prepared as described in EP-A-141927 or by analogous methods thereto.

Intermediates of the formula (IIIA) are known or are prepared by analogous methods, such as that described in Organic Syntheses Vol 60, page 66.

Intermediates of formula (IIIB) are known or prepared by analogous methods. The compound of formula (IIIB) wherein Q is bromo and $R_r$ is ethyl may be prepared from triethyl methanetricarboxylate according to the procedure described by H. Rapoport et.al., J. Org. Chem., 44. 3492(1979).

Intermediates of the formula (II) wherein Y is iodo or a thiobenzyl group may be prepared from the compound of formula (C). When Y is iodo, the preparation is by reaction with HI in a transhalogenation reaction, preferably using a cosolvent, such as acetone. When Y is optionally substituted thiobenzyl the preparation is by reaction with HY. When Y is (phenacylmethyl)thio the preparation is from thioguanine, by reaction with phenacyl bromide, as in Example 9a) hereinafter.

The following Examples illustrate the invention.

BRL 39123 and/or BRL 42810 may be prepared from the intermediates of Examples 2(a), 3(b), 4(b), 5(b), 6(b), 7, 8, and 9(b) according to the methods herein described.

EXAMPLE 1

(a)
9-(4-Acetoxy-3-acetoxymethylbut-1-yl)-2-amino-6-iodopurine

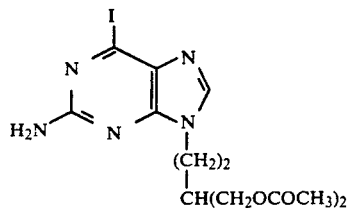

Preparation 1

2-Acetoxymethyl-4-iodobut-1-yl acetate (3.14 g) was added to a stirred suspension of 2-amino-6-iodopurine (2.61 g) and anhydrous potassium carbonate (2.08) in N,N-dimethylformamide (50 cm³) and the resulting mixture stirred at ambient temperature for 18 hours. T.l.c. (5% methanol-dichloromethane) showed two products, rf=0.24 and 0.47; corresponding to the N7- and N9-alkylated purines.

The reaction mixture was filtered and the residue washed with N,N-dimethylformamide (50 cm³). Evaporation of the filtrate gave a pale coloured solid. Purification via column chromatography on silica (100 g) [eluant 2.5% methanol-chloroform] gave the title compound 3.55 g (79.4%) and 0.4 g (8.9%) of the corresponding 7-isomer. m.p. (of title compound) 116°-170° C.

¹H n.m.r. (D₆DMSO): δ 1.90 (m, 3H,-CH₂CH-), 2.0 (s, 6H, CH₃-), 4.0(d,4H-OCH₂-), 4.10 (t, 2H, -NCH₂), 6.80(brs, 2H -NH₂), 8.15 (s, 1H, H-8).

Preparation 2

Using the above procedure 2-amino-6-iodopurine (3.8 g) and 2-acetoxymethyl-4-bromobut-1-yl acetate (4.4 g) gave the title compound 5.3 g (81%, m.p. 116°-117° C., and 0.5 g (11%) of the corresponding N-7-alkylated purine.

¹H n.m.r., t.l.c. and m.p. consistent with the title compound.

Preparation 3

A mixture 2-amino-6-iodopurine (1.5 g), 2-acetoxymethyl-4-chlorobut-1-yl acetate (1.41 g) and anhydrous potassium carbonate (1.19 g) in N,N-dimethylformamide (40 cm³) was stirred at 80° overnight. When cool the pale yellow mixture was filtered and the filtrate evaporated under reduced pressure. Purification via column chromatography on silica (150 g) [eluant 2% methanol-dichloromethane increasing to 4% methanol-dichloromethane] gave the title compound 2.08 g (81%) and 0.136 g (5.3%) of 7-(4-acetoxy-3-actetoxymethyl-but-1-yl)-2- amino-6-iodopurine.

¹H n.m.r., t.l.c. and m.p. consistent with the title compound.

Preparation 4

Potassium bromide (6.3 g) was added to a solution of 2-acetoxymethyl-4-methanesulphonyloxybut-1-yl acetate (10 g) in N,N-dimethylformamide (87 cm³) and the mixture stirred at 60°-70° for 2 hours. The reaction mixture was cooled to ambient temperature and 2-amino-6-iodopurine (9.1 g) and anhydrous potassium carbonate (7.3 g) added. The resulting suspension was stirred eat ambient temperature for 48 hours. T.l.c. (5% methanol-dichloromethane) showed two products. rf=0.24, and 0.47; corresponding to the N7- and N9-alkylated purines.

Filtration and evaporation of the filtrate gave a pale coloured residue that was partioned between water (500 cm³) and dichlormethane (500 cm³). The layers were separated and the aqueous phase re-extracted with dichlormethane (2×250 cm³). The combined organic extract was dried over magnesium sulphate and evaporated to give the crude product. Purification via silica gel chromatography (eluant 2% methanoldichloromethane increasing to 3% methanol-dichloromethane) gave the title compound 12.2 g (77%), m.p. 116°-117° C. and 0.8 g (5%) of 7-(4-acetoxy-3- acetoxymethylbut-1-yl)-2-amino-6-iodopurine.

(b)
9-(4-Acetoxy-3-acetoxymethylbut-1-yl)-2-aminopurine, (BRL42810)

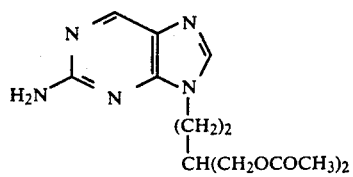

A solution of 9-(4-acetoxy-3-acetoxymethylbut-1-yl)-2-amino-6-iodopurine (15.3 g) and triethylamine (3.8 cm³) in ethanol (200 cm³) was hydrogenated over 5% palladium on charcoal (1.6 g, Englehard type 4573) at 50° and 50 psi for 4 hours. The reaction mixture was filtered and residue washed with ethanol (200 cm³). After evaporation of the filtrate to ca 50 cm³, water (150 cm³) and dichloromethane (75 cm³) was added. The phases were separated and the aqueous layer extracted with dichloromethane (3×75 cm³). The combined organic extract was dried over magnesium sulphate and evaporated to give the crude product. Recrystallisation from boiling butan-1-ol (30 cm³) gave the title compound 9.8 g (89%) m.p. 102° C.

¹H n.m.r. (CDCl₃) and t.l.c. (60:40 ethylacetate: methanol) were consistent with the title compound.

(c) 9-(4-Hydroxy-3-hydroxymethylbut-1-yl)quanine, (BRL39123)

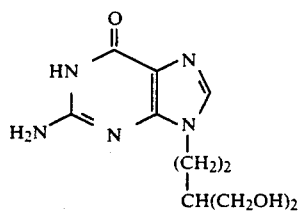

A mixture of 9-(4-acetoxy-3-acetoxymethylbut-1-yl)-2-amino-6-iodopurine (12 g) and 2M-hydrochloric acid (266 cm³) was stirred under reflux for 3 hours. After cooling, a solution of sodim hydroxide (36 g) in water (72 cm³) was added and the stirring continued at ambient temperature for 2 hours. The solution was neutralized with concentrated hydrochloric acid to precipitate the product. Recrystallization from boiling water gave the title compound 6.0 g (88%), m.p. 278°–280° C. (dec.).

¹H n.m.r. (D₆DMSO): δ 1.50 (m, 1H,-C$\underline{H}$<), 1.75 (q, 2H C$\underline{H}$₂-CH), 3.45 (m, 4$\underline{H}$, -C$\underline{H}$₂OH), 4.05 (t, 2H, -NC$\underline{H}$₂-), 4.50 (t, 2H, -CH₂O$\underline{H}$), 6.50 (brs, 2H, -N$\underline{H}$₂), 7.75 (s, 1H, $\underline{H}$-8), 10.75 (brs, 1H, -N$\underline{H}$CO).

EXAMPLE 2

(a)
9-(4-Acetoxy-3-acetoxymethylbut-1-yl)-2-amino-6-[(phenylmethyl)thio]purine

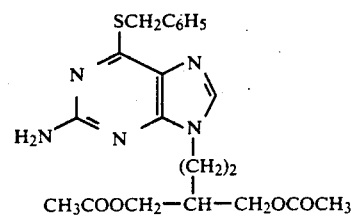

A mixture of 2-amino-6[(phenylmethyl)thio]purine (1)(20 g), 2-acetoxymethyl-4-iodobut-1-yl acetate (24.5 g) and potassium carbonate (16.3 g) in N,N-dimethylformamide (250 cm³) was stirred at ambient temperature for 66 hours. T.l.c. (5% methanol-dichloromethane) showed two spots, rf 0.44, 0.74. The reaction mixture was filtered and the residue washed with N,N-dimethylformamide (100 cm³). Evaporation of the filtrate gave a pale yellow viscous gum.

Purification via silica gel chromatography (eluant 5% methanol-dichloromethane) gave the title compound 30 g (87%), rf (5% methanol-dichloromethane)=0.74, as a viscous gum. A small amount of the corresponding N7-isomer 2.4 g (7%) was also isolated, rf (5% methanol-dichloromethane)=0.44.

¹H n.m.r. (CDCl₃): δ1.85(m, 3H,-C$\underline{H}$₂-C$\underline{H}$-), 2.05(s,6H,C$\underline{H}$₃), 4.10(m,6H,NC$\underline{H}$₂+OC$\underline{H}$₂-), 4.55(s,2H,C$\underline{H}$₂C₆H₅), 5.15(brs,2H,NH₂), 7.25(m,3H,C₆$\underline{H}$₅), 7.40(d,2H,C₆$\underline{H}$₅), 7.65(s,1H, $\underline{H}$-8).

(b)
9-(4-Acetoxy-3-acetoxymethylbut-1-yl)-2-aminopurine, (BRL 42810)

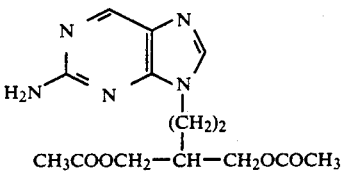

Raney nickel (4 g) was added to a solution of 9-(4-acetoxy-3-acetoxymethylbut-1-yl)-2-amino-6-[(phenylmethyl)thio]purine (10 g) in ethanol (250 cm³) and the mixture treated with hydrogen (100 psi) at 100° for 2 hours.

After filtration and washing of the residue with ethanol (250 cm³) evaporation of the filtrate gave the crude material. Recrystallisation from butan-1-ol (10 cm³) gave BRL 42810, 5.1 g (70%), m.p. 102°. This material was consistent with that prepared previously.

¹H n.m.r. (CDCl₃) δ1.90(m, 3H,-C$\underline{H}$₂CH-), 2.00(s,6H,-C$\underline{H}$₃), 4.05 (d,4H,OC$\underline{H}$₂-), 4.10(t,2H,NC$\underline{H}$₂-), 5.35(brs, 2H,NH₂), 7.70(s,1H,$\underline{H}$-8), 8.60(s,1H,$\underline{H}$-6).

EXAMPLE 3

(a) 2-Amino-6-[(4-methylphenyl)methylthio]purine

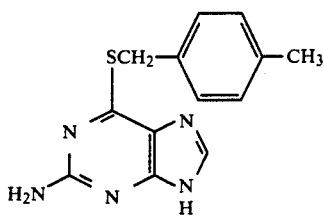

A mixture of thioguanine (25 g), c-chloro-p-xylene (21 g) and potassium carbonate (30 g) in N,N-dimethylformamide (500 cm³) was stirred at ambient temperature overnight. The reaction mixture was filtered and the filtrate evaporated to give a yellow solid. Recrystallization from methanol (100 cm³) gave 25.7 g (64%) of the title compound, m.p. 240°-242° C.

¹H n.m.r. (D⁶DMSO): δ 6 2.25 (s, 3H, -C$\underline{H}_3$), 4.50 (s, 2H, SC$\underline{H}_2$-), 6.45 (brs, 2H, -N$\underline{H}_2$), 7.10 (d, 2$\underline{H}$, C$_6\underline{H}_4$-), 7.35 (d, 2H, C$_6\underline{H}_4$), 7.90 (s, 1H, $\underline{H}$-8), 12.55 (brs, 1H, >N$\underline{H}$).

(b) 9-(4-Acetoxy-3-acetoxymethylbut-1-yl)-2-amino-6-[(4-methylphenyl)methylthio]purine

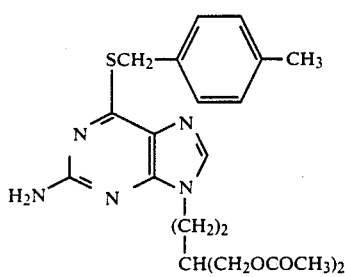

Using the previously described procedure 2-amino-6-[(4-methylphenyl)methylthio]purine (25 g) and 2-acetoxymethyl-4-iodobut-1-yl acetate (29 g) gave the title compound 33.3 g (79%) m.p. 102°-103°, and 4.2 g (9.9%) of 7-(4-acetoxy-3-acetoxymethylbut-1-yl)-2-amino-6-[(4-methylphenyl)methylthio]purine ¹H n.m.r. (D⁶DMSO) of the title compound: δ 1.85 (m, 3H, -C$\underline{H}_2$C$\underline{H}$<), 2.00 (s, 6H, C$\underline{H}_3$CO-), 2.25 (s, 3H, -C$\underline{H}_3$), 4.00 (d, 4H, -OC$\underline{H}_2$-), 4.10 (t, 2H, -NC$\underline{H}_2$), 4.50 (s, 2H, -SC$\underline{H}_2$), 6.60 (brs, 2H, -N$\underline{H}_2$), 7.10 (d, 2$\underline{H}$, C$_6\underline{H}_4$) 7.30 (d, 2$\underline{H}$, C$_6\underline{H}_4$), 7.95 (s, 1H, $\underline{H}$-8).

(c) 9-(4-Acetoxy-3-acetoxymethylbut-1-yl)-2-aminopurine, (BRL42810)

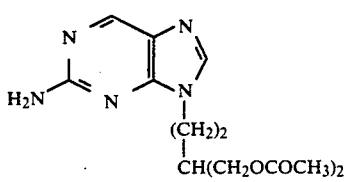

Raney nickel (3 g) was added to a solution of 9-(4-acetoxy-3-acetoxymethylbut-1-yl)-2-amino-6-[(4-methylphenyl)methylthio]purine (10 g) in ethanol (250 cm³) and the mixture treated with hydrogen at 100° and 100 psi for 40 hours. Filtration and evaporation of the filtrate gave the crude compound. Recrystallization from butan-1-ol (18 cm³) gave the title compound 4.2 g (60%). m.p. 100°-102° C.

¹H n.m.r. (CDCl₃) and t.l.c (60:40 ethylacetate: methanol) were consistent with the title compound.

EXAMPLE 4

(a) 2-Amino-6-[(diphenylmethyl)thio]purine

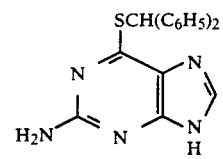

A mixture of thioguanine (25 g), bromodiphenylmethane (37.1 g) and potassium carbonate (31.1 g) in N,N-dimethylformamide (250 cm³) was stirred at ambient temperature for 66 hour. The reaction mixture was filtered and the filtrate evaporated to give a cream solid. Recrystallisation from methanol gave 24 g (48%) of the title compound, m.p. 226°-227° C.

¹H n.m.r. (D₆DMSO): δ 6.35 (s, 2H, -N$\underline{H}_2$), 6.70 (s, 1H, SC$\underline{H}$<), 7.30 (m, 6H, C$_6\underline{H}_5$-), 7.50 (d, 4H, C$_6\underline{H}_5$-), 7.90 (s, 1H, $\underline{H}$-8), 12.50 (brs, 1H, >N-$\underline{H}$).

(b) 9-(4-Acetoxy-3-acetoxymethylbut-1-yl)-2-amino-6-[(diphenylmethyl)thio]purine

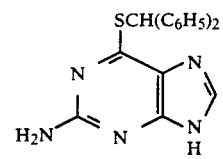

A mixture of 2-amino-6-[(diphenylmethyl)thio]purine (6.7 g), 2-acetoxymethyl-4-iodobut-1-yl acetate (7.0 g) and anhydrous potassium carbonate (4.14 g) in N,N-dimethylformamide (100 cm³) was stirred at ambient temperature overnight. The reaction mixture was filtered and the residue washed with N,N-dimethylformamide (100 cm³). Evaporation of the filtrate gave a pale coloured oil. Purification via column chromatography on silica (450 g) [eluant 3% methanol-dichloromethane] gave the title compound 9.3 g (89%) as a viscous gum and 1.1 g (10.5%) of 7-(4-acetoxy-3-acetoxymethylbut-1-yl)-2-amino-6-(diphenylmethyl)thio]purine.

¹H n.m.r. (CDCl₃) of the title compound δ 1.85 (m, 3H, -C$\underline{H}_2$C$\underline{H}$<), 2.05 (s, 6H, C$\underline{H}_3$) 4.15 (d, 6H, -NC$\underline{H}_2$+-OC$\underline{H}_2$-), 5.2 (s, 2H, -N$\underline{H}_2$) 6.2 (s, 1H, -SC$\underline{H}$<) 7.25 (m, 6H, C$_6\underline{H}_5$-), 7.5 (d, 4H, C$_6\underline{H}_5$), 7.65 (s, 1H, $\underline{H}$-8)

Mass spectrum of the title compound : m/e 519 (m⁺), main fragment ions at 277, 255, 199, 167 and 91.

EXAMPLE 5

(a) 2-Amino-9-(ethyl 2,2-dicarboethoxybutanoate-4-yl)-6-[(phenylmethyl)thio]purine

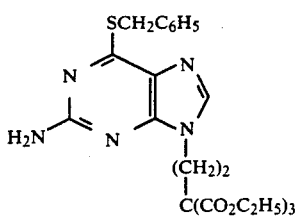

Ethyl 4-bromo-2,2-dicarboethoxybutanoate (14.5 g) was added to a stirred suspension of 2-amino-6-[(phenylmethyl)thio]purine (11.4 g) and anhydrous potassium carbonate (9.15 g) in N,N-dimethylformamimde (100 cm³) and the resulting mixture stirred at 40° overnight. When cool the mixture was filtered and the filtrate evaporated to give a pale coloured viscous gum. Purification via silica gel chromatography (eluant dichloromethane increasing to 10% methanoldichloromethane) gave 11.42 g (50%) of the title compound, m.p. 100°–102°. A second compound, 5.38 g was identified as 2-amino-9-(ethyl 2-carboethoxybutanoate-4-yl)-6-[(phenylmethyl)thio]purine, m.p. 86°–88°. A mixed fraction containing 2.15 g of the corresponding N7-substituted di- and tri- carboethoxybutanoates was also isolated.

¹H n.m.r. (CDCl₃) of the title compound: δ 1.25(t, 9H, -CH₃), 2.65(t, 2H, -CH₃C -), 4.25 (m, 8H, -NCH₂- +-CH₂CH₃), 4.55 (s, 2H, -SCH₂-) 5.10(brs, 2H, -NH₂), 7.25(m, 3H, C₆H₅-), 7.40 (d,2H, C₆H₅-), 7.609(s, 1H, H-8).

(b) 2-Amino-9-(ethyl 2-carboethoxybutanoate-4-yl)-6-[(phenylmethyl)thio]purine

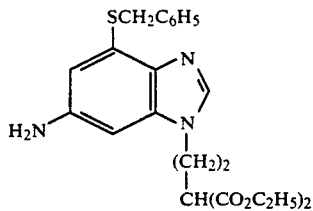

2-Amino-9-(ethyl 2,2-dicarboethoxybutanoate-4-yl)-6-[(phenylmethyl)thio]purine (3 g) was added to a solution of sodium (0.4 g) in ethanol (20 cm³) and the mixture stirred at ambient temperature for 15 minutes. T.l.c. (2% methanol-dichloromethane), one-spot rf 0.40. The solution was neutralized with 2M-hydrochloric acid and water (100 cm³) added. The mixture was extracted with dichloromethane (2×50 cm³) and the extract dried over magnesium sulphate. Filtration and evaporation of the filtrate gave the crude material. Purification via column chromatography on silica (40 g) [eluant dichloromethane increasing to 5% methanol-dichloromethane] gave the title compound 1.2 g (46.5%) as a viscous gum which slowly crystallized on standing at ambient temperature, m.p. 86°–88°.

¹H n.m.r. (CDCl₃) δ 1.25 (t, 6H, CH₃), 2.30 (m, 2H, CHCH₂-), 3.20(t, 1H, CCHC), 4.00 (m, 6H, -NCH₂+-CH₂CH₃), 4.40(s, 2H, SCH₂-), 5.50 (brs, 2H, -NH₂), 7.10(q, 3H, C₆H₅), 7.25 (d, 2H, C₆H₅-), 2.50 (s, 1H, H-8).

EXAMPLE 6

(a) 2-Amino-9-(ethyl 2,2-dicarboethoxybutanoate-4-yl)-6-iodopurine

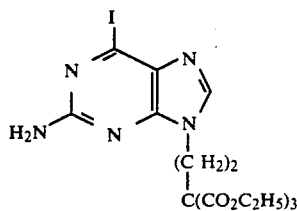

A mixture of 2-amino-6-iodopurine (10 g), ethyl 4-bromo-2,2-dicarboethoxybutanoate (13 g) and anhydrous potassium carbonate (8.0 g) in N,N-dimethylformamide (150 cm³) was stirred at 40° overnight. The mixture was filtered and the filtrate evaporated to leave a pale yellow solid. The solid was dissolved in 2% methanol-dichloromethane and column chromatographed on silica (200 g) [eluant=2% methanol-dichloromethane] to give the title compound 13.8 g (69.4%) and 1.5 g (7.5%) of 2-amino-7-(ethyl 2,2-dicarboethoxybutanoate-4-yl)-6-iodopurine.

m.p. (of title compound) 99°–102°

¹H n.m.r. (D⁶ -DMSO) of title compound: δ1.20(t, 9H, -CH₂CH₃), 2.60 (t, 2H, -CH₂C-), 4.15(q, 6H, -CH₂CH₃), 4.50(t, 2H, N-CH₂), 6.80(brs, 2H, -NH₂), 8.00(s, 1H, H-8).

(b) 2-Amino-9-(ethyl 2,2-dicarboethoxybutanoate-4-yl)purine

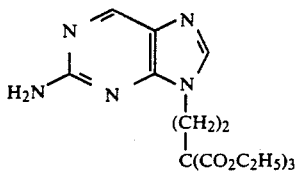

A mixture of 2-amino-9-(ethyl 2,2-dicarboethoxybutanoate-4-yl)-6-iodopurine (85 g), triethylamine (25.25 cm³) and 5% palladium on charcoal (10 g) in ethanol (1,500 cm³) was hydrogenated at 100 psi and 50° for 2 hours. T.l.c. (10% methanol-chloroform) showed one spot, rf=0.40. When cool the mixture was filtered and the filtrate evaporated to leave a solid. The solid was dissolved in water (1000 cm³) and extracted with chloroform (3×500 cm³). The organic extracts were combined, dried over magnesium sulphate and evaporated to give the title compound 62.2 g (96%) as an oil which crystallized on standing.

¹H n.m.r. (D⁶ -DMSO): 1.20(t,9H, -CH₂CH₃), 2.65(t,2H, -CH₂C-), 4.15(q,6H, -CH₂CH3), 4.35(t,2H, N-CH₂), 6.50(brs, 2H, -NH₂), 7.95(s, 1H,H-8), 8.65(s, 1H, H-6).

EXAMPLE 7

2-Amino-9-1-(2,2-dimethyl-1,3-dioxane-4,6-dione-5-yl)eth-2-yl]-6-[(phenylmethyl)thio1purine

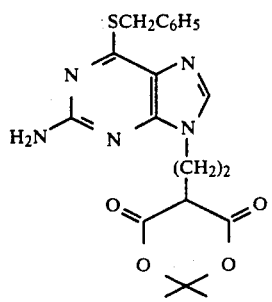

A mixture of 2-amino-6-[(phenylmethyl)thio]purine (1.0 g), 2,2-dimethyl-1,3-dioxaspiro[2.5]octane-4,6dione (0.7 g) and potassium carbonate (1.0 g) in dry N,N-dimethylformamide (10 cm³) was stirred at ambient temperature for 18 hours. The mixture was filtered and the filtrate evaporated. T.l.c. (20% methanoldichloromethane) showed two products, rf=0.3 and 0.1, corresponding to the potassium salts of the title compound and the N-7 isomer respectively. Proton n.m.r. evidence suggested a product ratio of 2.7:1.

The residue was dissolved in water, acidified to pH 4 with dilute hydrochloric acid and extracted with dichloromethane (2×100 cm³). The organic layers were combined, dried (magnesium sulphate) and evaporated to give a yellow solid.

Purification by column chromatography on silica [eluant =5% methanol-dichloromethane] gave the title compound that was recrystallized from boiling ethyl acetate (0.2 g, 12%).

$^1$H n.m.r. (D$^6$-DMSO): δ1.68(s, 3H, -CH$_3$), 1.83(s, 3H, -CH$_3$), 2.39(m, 2H, H-2'), 4.26(m, 2H, H-1'), 4.50(m, 1H,H-3'), 4.56(s, 2H, -CH$_2$C$_6$H$_5$), 6.54(brs, 2H, -NH$_2$), 7.19–7.49 (m, 5H, -C$_6$H$_5$), 7.95(s, 1H, H-8).

C$_{20}$H$_{21}$N$_5$O$_4$S requires: C,56.19; H,4.95; N,16.38%. found: C,55.97; H,4.94; N,16.04%.

EXAMPLE 8

2-Amino-6-iodo-9-[1-(2,2-dimethyl-1,3-dioxane-4,6-dione-5-yl)eth-2-yl]purine potassium salt

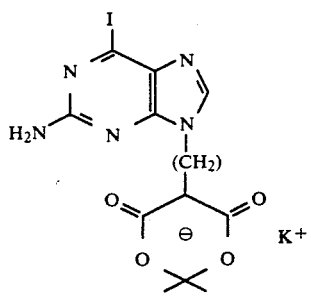

A mixture of 2-amino-6-iodopurine (1.3 g), 2,2-dimethyl-1,3-dioxaspiro[2.5]octane-4,6-dione (0.85 g) and potassium carbonate (1.2 g) in N,N-dimethylformamide (20 cm³) was stirred at ambient temperature for 18 hours. The mixture was filtered and the solvent evaporated. Proton n.m.r. spectroscopy suggested a mixture of the title compound and 2-amino-6-iodo-7-[1-(2,2-dimethyl-1,3-dioxane-4,6-dione-5-yl)eth-2-yl]purine potassium salt in the ratio of 2.8:1.

$^1$H n.m.r. (D$^6$-DMSO): of the title compound: δ1.40(s, 6H, -CH$_3$), 2.64(t, 2H, H-2'), 4.04(t, 2H, H-1'), 6.75(brs, 2H, -NH$_2$), 7.96(s, 1H, H-8).

EXAMPLE 9

(a) 2-Amino-6-[(phenacylmethyl)thio]purine

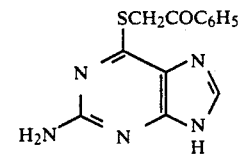

A mixture of thioguanine (8.36 g), phenacyl bromide (9.95 g) and potassium carbonate (7.60 g) in N,N-dimethylformamide (100 cm³) was stirred at ambient temperature for 20 hours. The reaction mixture was filtered and the filtrate evaporated to give a cream solid. Recrystallisation from boiling methanol (100 cm³) gave 10.3 g (72.2%) of the title compound m.p. 204°–205° C.

$^1$H n.m.r. (D$_6$DMSO): δ 5.10 (s, 2H, -SCH$_2$), 6.30 (s, 2H, -NH$_2$), 7.65 (t, 2H, C$_6$H$_5$-), 7.80 (m, 1H, C$_6$H$_5$-), 8.05 (s, 1H, H-8), 8.20 (d, 2H, C$_6$H$_5$-).

Mas spectrum of the title compound $^m$/p 285(m$^+$), main fragment ions at 253, 225, 180, 134, 105 and 77.

(b) 9-((4-Acetoxy-3-acetoxymethylbut-1-yl)-2-amino-6-[(phenacylmethyl)thio]purine

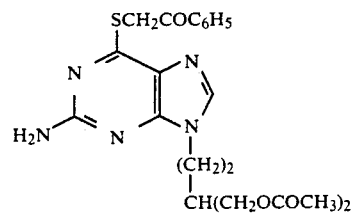

Using the previously described procedure 2-amino-6-[(phenacylmethyl)thio]purine (5.71 g) and 2-acetoxymethyl-4-iodobut-1-yl acetate (6.93 g) gave the title compound 7.3 g (77.4%) m.p. 130°–131° and 0.7 g (7.4%) of 7-(4-acetoxy-3-acetoxymethylbut-1-yl)-2-amino-6-[(phenacylmethyl)thio]purine.

$^1$H n.m.r. (CDCl$_3$) of the title compound: 1.90 (m, 3H, -CH$_2$CH<), 2.10 (s, 6H, CH$_3$CO), 4.15 (m, 6H, -NCH$_2$+-OCH$_2$<), 4.70 (bs, 4H, -NH$_2$+-SCH$_2$-), 7.55 (m, 3H, C$_6$H$_5$-), 7.65 (s, 1H, H-8), 8.10 (d, 2H, C$_6$H$_5$-).

Mass spectrum of the title compound: $^m$/e 471 (m$^+$), main fragment ions at 439, 411, 366, 294, 180, 105 and 77.

We claim:

1. A process for preparation of a compound of formula (I) or a pharmaceutically acceptable salt thereof:

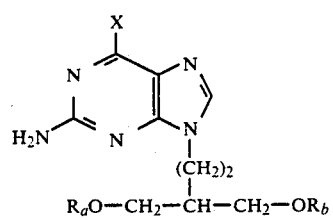

wherein $R_a$ and $R_b$ are independently hydrogen or a group RCO- wherein R is phenyl or $C_{1-18}$ alkyl, which process comprises reacting a compound of formula (II):

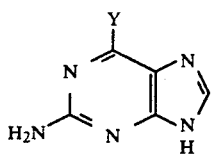
(II)

wherein the amino group is optionally protected, Y is iodo, optionally substituted benzylthio optionally substituted by $C_{1-4}$ alkyl, halo or $C_{1-4}$ alkoxy or (phenyacylmethyl)thio, with a compound of formula (III):

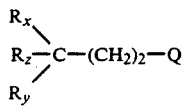
(III)

wherein Q is a leaving group, $R_x$ and $R_y$ are protected hydroxymethyl or acyloxymethyl wherein the acyl moiety is —RCO— in which R is phenyl or $C_{1-18}$ alkyl, or group(s) convertible to hydroxymethyl or acyloxymethyl wherein the acyl moiety is —RCO— in which R is phenyl, or $C_{1-18}$ alkyl; and $R_z$ is hydrogen or a group convertible thereto; and thereafter converting Y to X is hydroxy by means of hydrolysis, or to X is hydrogen by means of reduction; converting $R_x$ and $R_y$ when other than hydroxymethyl or acloxymethyl wherein the acyl moiety is —RCO— in which R is phenyl or $C_{1-18}$ alkyl, to hydroxymethyl or acyloxymethyl wherein the acyl moiety is —RCO— in which R is phenyl or $C_{1-18}$ alkyl, optionally converting $R_x/R_y$ hydroxymethyl or acyloxymethyl wherein the acyl moiety is —RCO— in which R is phenyl or $C_{1-18}$ alkyl or vice versa, deprotecting the 2-amino group where necessary and converting $R_z$, (when other than hydrogen) to hydrogen; and optionally forming a pharmaceutically acceptable salt thereof.

2. A process according to claim 1 wherein the compound of formula (III) is of formula (IIIA) or (IIIB):

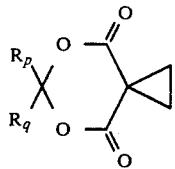
(IIIA)

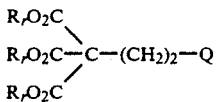
(IIIB)

wherein $R_p$ and $R_q$ are independently hydrogen, $C_{1-6}$ alkyl or phenyl, or $R_p$ and $R_q$ together are $C_{4-6}$ polymethylene; and $R_r$ is $C_{1-6}$ alkyl or phenyl $C_{1-6}$ alkyl, in which any phenyl moieties are optionally substituted by iodo, benzylthio optionally substituted by $C_{1-4}$ alkyl, halo, $C_{1-4}$ alkoxy or (phenacylmethyl)thio.

3. A process according to claim 2 wherein the compound of formula (III) is of formula (III)':

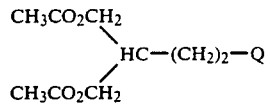
(III)' wherein Q is as defined in claim 1.

4. A process according to claim 1 wherein Y is iodo.

5. A process according to claim 1 wherein Q is halo, tosyloxy or mesyloxy.

6. A process according to claim 1 for the preparation of a compound of formula (A) or (B):

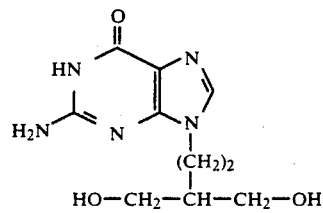
(A)

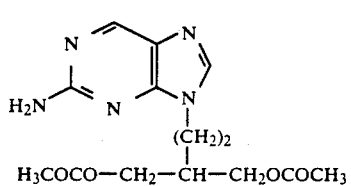
(B)

7. An intermediate of formula (IV):

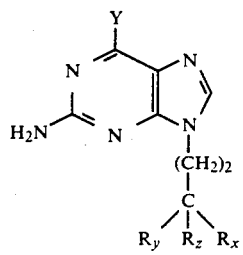
(IV)

wherein Y, $R_x$, $R_y$ and $R_z$ are as defined in claim 1.

8. 9-(4-Acetoxy-3-acetoxymethylbut-1-yl)-2-amino-6-iodopurine,
9-(4-acetoxy-3-acetoxymethylbut-1-yl)-2-amino-6-[(phenylmethyl)thio]purine,
9-(4-acetoxy-3-acetoxymethylbut-1-yl)-2-amino-6-[(4-methylphenyl)methylthio]purine,
9-(4-acetoxy-3-acetoxymethylbut-1-yl)-2-amino-6[(diphenylmethyl)thio]purine,
2-amino-9-(ethyl 2,2-dicarboethoxybutanoate-4-yl)-6[(phenylmethyl)thio]purine,
2-amino-9-(ethyl 2,2-dicarboethoxybutanoate-4-yl)-6iodopurine,
2-amino-9-[1-(2,2-dimethyl-1,3-dioxane-4,6-dione-5-yl)eth-2-yl]-6-[(phenylmethyl)thio]purine,
2-amino-6-iodo-9-[1-(2,2-dimethyl-1,3-dioxane-4,6-dione-5-yl)eth-2-yl]purine potassium salt, or
9-((4-acetoxy-3-acetoxymethylbut-1-yl)-2-amino-6-[(phenacylmethyl)thio]purine.

* * * * *